US005556859A

United States Patent [19]
Johnson

[11] Patent Number: 5,556,859
[45] Date of Patent: Sep. 17, 1996

[54] N-(4-PYRIMIDINYL)AMIDE PESTICIDES

[75] Inventor: Peter L. Johnson, Indianapolis, Ind.

[73] Assignee: DowElanco, Indianapolis, Ind.

[21] Appl. No.: 362,049

[22] Filed: Dec. 22, 1994

[51] Int. Cl.$^6$ .................. A61K 31/505; C07D 239/42
[52] U.S. Cl. .................. 514/256; 514/269; 514/275; 544/60; 544/122; 544/243; 544/296; 544/315; 544/319; 544/326; 544/329; 544/330
[58] Field of Search .................. 514/256, 269, 514/275; 544/243, 60, 122, 319, 326, 329, 330, 315, 296

[56] References Cited

FOREIGN PATENT DOCUMENTS 0519211  12/1992  European Pat. Off. .................. 544/329
9208704   5/1992  WIPO .................. 544/329

OTHER PUBLICATIONS

Derwent Abstract 90–165395/22 (1991) corresponding to JO 3007–267–OA and EP 370704A.
Chemical Abstracts 113:212005g (1990) corresponding to EP 370704A.
Derwent Abstract 86–266341/41 (1990) corresponding to JO 2209–874–A and EP 196534A.
CA Selects:Fungicides, issue 18, 1991, abstract 115:92287t, corresponding to EP 424125A.
Derwent Abstract 91–119354/17 (1991) corresponding to EP 424,125A.
Derwent Abstract 91–038550/06 (1991) corresponding to EP 411,634A.
CA Selects:Fungicides, issue 13, 1991, p. 7, abst. 114:247303a, abstracting EP 411,634A (UBE).
Derwent Abstract 88–106970/16 (1993) abstracting EP 264217B (UBE).
Derwent Abstract 91–054754/08 (1991) abstracting JO 3005–466–A (UBE).
Derwent Abstract 91–054761/08 (1991) abstracting JO 3005–476–A (UBE).
Derwent Abstract 90–11957/15 (1990) abstracting JO 2062–867–A (UBE).
Derwent Abstract 91–122587/17 (1991) abstracting JO 3063–266–A (UBE).
Derwent Abstract 91–122589/17 (1991) abstracting JP 3063–271–A (UBE).
Derwent Abstract 93–16909/21 (1993) abstracting EP 543,402A (UBE).
CA Selects:Fungicides, issue 10, 1991, p. 3, abst. 114:180362y, abstracting JP 02,300,176 (UBE).
CA Selects:Insecticides, issue 17, 1990, p. 10, abst. 113:59210y, abstracting EP 356,158A (UBE).
CA Selects:Fungicides, issue 2, 1990, p. 5, abst. 112:21012b, abstracting EP 323,757 (UBE).
Chemical Abstracts, 113:59210 (1990) abstracting EP 356, 158A (UBE).

Derwent Abstract 88–106970/16 (1991) abstracting U.S. Pat. No. 4,985,426.
Derwent Abstract 92–2001100/24 (1992) abstracting WO 9208704–A1 (Dupont).
CA Selects:Insecticides, issue 17, 1992, p. 13, abst. 117:69881q, abstracting WO 92 08,704 (Dupont).
Derwent Abstract 91–119531/17 (1991) abstracting EP 424, 317A (Ciba–Geigy).
Derwent Abstract 84–086099/14 (1992) abstracting JP 2024351B (Sankyo).
PCT/US92/10331, filed Jan. 12, 1992 by DowElanco et al. on "N–(5–Isothiazolyl) Amide Pesticides".
Derwent Abstract 93–100559/12 (1993) abstracting EP 556381A, corresponding to U.S. Ser. No. 07/932,405 (Dow-Elanco).
Derwent Abstract 92–053942/07 (1992) abstracting JO 4001–180–A (Mitsubishi).
Derwent Abstract 93–296162/38 (193) abstracting DE 4208254–A1 (Hoechst).
Derwent Abstract 93–102504/13 (1993) abstracting WO 9306091–A1 (Hoechst).
Derwent Abstract 93–172659/21 (1993) abstracting JP 05105671–A (Sumitomo).
Beeley et al., Chemical Abstracts, vol. 120, entry 269853f (1993).
Maienfisch et al., Chemical Abstracts, vol. 119, entry 95550s (1993).
Wada et al., Chemical Abstracts, vol. 114, entry 101916f (1991).
Wada et al., Chemical Abstracts, vol. 107, entry 175976c (1987).
Aries, Chemical Abstracts, vol. 76, entry 140543y (1972).
Aries, Chemical Abstracts, vol. 76, entry 140256g (1972).
Aries, Chemical Abstracts, vol. 72, entry 111504y (1970).
Aries, Chemical Abstracts, vol. 72, entry 43716s (1970).

*Primary Examiner*—Yogendra N. Gupta
*Attorney, Agent, or Firm*—Donald R. Stuart

[57] ABSTRACT

N-(4-Pyrimidinyl)amide pesticides of the formulas and N-oxides and salts thereof, wherein the variable groups are as defined in the specification, are active against nematodes, insects, mites, and plant pathogens.

10 Claims, No Drawings

N-(4-PYRIMIDINYL)AMIDE PESTICIDES

This invention provides new compounds that are useful as nematicides, insecticides, miticides, and plant fungicides. The invention also provides nematicidal, insecticidal, miticidal, and fungicidal methods.

There is an acute need for new nematicides, insecticides, miticides, and plant fungicides. Available nematicides typically have high mammalian toxicity and must be used at high rates. A nematicide that can be applied at lower rates and that has lower mammalian toxicity would represent a significant advance.

Mites and insects are developing resistance to the miticides and insecticides in current use. Resistance to insecticides in anthropods is widespread, with at least 400 species resistant to one or more insecticides. The development of resistance to some of the older insecticides, such as DDT, the carbamates, and the organophosphates is well known. But resistance has even developed to some of the newer pyrethroid insecticides and miticides. Similarly, target pathogens are rapidly developing resistance to currently used fungicides. At least 50 species of fungi have developed resistance to the benzimidazole fungicides. Even recently introduced fungicides, like the acylalanines, which initially exhibited excellent control of potato late blight and grape downy mildew in the field, have become less effective because of resistance. Therefore a need exists for new insecticides, miticides, and fungicides, and particularly for compounds that have new or atypical modes of action.

This invention provides compounds of the formula (1) and (2):

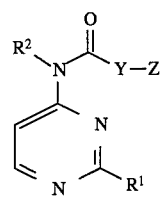 (1)

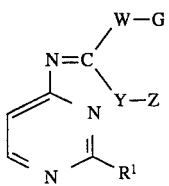 (2)

and N-oxides and salts thereof, wherein $R^1$ is H, $(C_1-C_4)$alkyl, $(C_3-C_4)$ branched alkyl, $(C_3-C_7)$ cycloalkyl, $(C_2-C_4)$ alkenyl, $(C_3-C_4)$ branched alkenyl, halo$(C_1-C_4)$alkyl, $(C_1-C_4)$alkoxy, $(C_1-C_4)$alkoxy$(C_1-C_4)$alkyl, halo$(C_1-C_4)$alkoxy, $(C_1-C_4)$alkylthio, $(C_1-C_4)$alkylsulfonyl, $(C_1-C_4)$alkylsufinyl, halo, or phenyl;

$R^2$ is H, $(C_1-C_4)$alkyl, $(C_3-C_4)$ branched alkyl, $(C_1-C_4)$alkanoyl, halo$(C_1-C_4)$alkyl, $(C_1-C_4)$alkoxymethyl, $CH_2SiR^9R^{10}R^{11}$, hydroxymethyl, benzyl, $(C_3-C_6)$cycloalylmethyl,

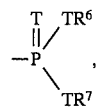

where $R^9$, $R^{10}$ and $R^{11}$ are independently $(C_1-C_4)$ alkyl, $(C_3-C_4)$ branched alkyl, phenyl, or substituted phenyl, each T is independently O or S, and $R^6$ and $R^7$ are independently $(C_1-C_4)$ alkyl, $(C_3-C_4)$ branched alkyl, phenyl, or substituted phenyl;

Y is (1) —$CH_2$—, optionally substituted with $(C_1-C_4)$ alkyl, $(C_2-C_4)$ alkenyl, $(C_2-C_4)$ alkynyl, branched $(C_3-C_7)$ alkyl, $(C_3-C_7)$ cycloalkyl, $(C_3-C_7)$ cycloalkenyl, halo, halo $(C_1-C_4)$alkyl, halo $(C_1-C_4)$ alkoxy, hydroxy, CN, $(C_1-C_4)$ alkanoyl, $(C_1-C_4)$ alkoxycarbonyl, aryloxycarbonyl, where aryl is as defined below, hydroxy $(C_1-C_4)$ alkyl, $(C_1-C_4)$ alkoxy $(C_1-C_4)$ alkyl, or (2)

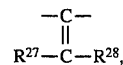

where $R^{27}$ and $R^{28}$ are independently selected from H, $(C_1-C_4)$ alkyl, $(C_1-C_4)$ alkoxy, SH, S-lower alkyl, $NH_2$, NH-lower alkyl, N,N-di-lower alkyl, O-lower alkyl, OH, morpholino, piperidinyl, pyrrolidinyl, thiomorpholino, or $R^{27}$ and $R^{28}$ combine to form part of a $(C_5-C_6)$ saturated or unsaturated ring optionally including 1 or 2 hetero atoms selected from O, S, or $NR^5$, where $R^5$ is H, $(C_1-C_4)$alkyl, or $(C_1-C_4)$alkanoyl;

Z is (1) $(C_3-C_8)$ cycloalkyl or cycloalkenyl, optionally substituted with one or more groups independently selected from $(C_1-C_4)$ alkyl, $(C_1-C_4)$ alkoxy, halo $(C_1-C_4)$ alkyl, halo $(C_1-C_4)$ alkoxy, halo, hydroxy, or $(C_1-C_4)$ alkanoyl; or (2) aryl, where aryl is (a) a phenyl group optionally substituted with one or more groups independently selected from:
halo,
$(C_3-C_8)$ cycloalkyl,
$(C_3-C_8)$ cycloalkenyl,
phenoxy,
substituted phenoxy,
phenylthio,
substituted phenylthio,
phenyl,
substituted phenyl,

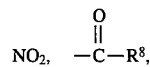

where $R^8$ is $(C_1-C_7)$ alkyl, halo $(C_1-C_7)$ alkyl, $(C_3-C_7)$ branched alkyl, halo $(C_3-C_7)$ branched alkyl, $(C_3-C_7)$ cycloalkyl, halo $(C_3-C_7)$ cycloalkyl, $(C_1-C_7)$ alkoxy, hydroxy, phenyl, substituted phenyl, phenoxy, or substituted phenoxy,

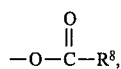

wherein $R^8$ is defined as above, except that hydroxy is excluded,

OH,

CN, $SiR^9R^{10}R^{11}$ or $OSiR^9R^{10}R^{11}$, where $R^9, R^{10}$ and $R^{11}$ are independently $(C_1-C_4)$ alkyl, $(C_3-C_4)$ branched alkyl, phenyl, or substituted phenyl, $NR^{12}R^{13}$, where $R^{12}$ and $R^{13}$ are independently H, $(C_1-C_4)$ alkyl, or $(C_1-C_4)$ alkanoyl, $S(O)R^{14}$, $SO_2R^{14}$, or $OSO_2R^{14}$, where $R^{14}$ is $(C_1-C_{10})$ alkyl, phenyl, or substituted phenyl;

a $(C_1-C_{12})$ saturated or unsaturated hydrocarbon chain, straight chain or branched optionally including a hetero atom selected from O, S, SO, $SO_2$, $NR^5$, or $SiR^6R^7$, where $R^5$, $R^6$ and $R^7$ are as defined above, and optionally substituted with halo, halo $(C_1-C_4)$ alkoxy, hydroxy, $(C_3-C_8)$ cycloalkyl or cycloalkenyl, $(C_1-C_4)$ alkanoyl, phenoxy, substituted phenoxy, phenyl, substituted phenyl, phenylthio, substituted phenylthio, or cyano;

$(C_1-C_7)$ alkoxy optionally substituted with halo, phenyl, substituted phenyl, $(C_3-C_8)$ cycloalkyl or cycloalkenyl, phenoxy, or substituted phenoxy; or $(C_1-C_7)$ alkylthio optionally substituted with halo, phenyl, substituted phenyl, $(C_3-C_8)$ cycloalkyl or cycloalkenyl, phenoxy or substituted phenoxy;

b) a furyl group of formula (3)

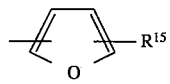

(3)

where $R^{15}$ is H, halo, halomethyl, CN, $NO_2$, $(C_1-C_4)$ alkyl, $(C_3-C_4)$ branched alkyl, phenyl, $(C_1-C_4)$ alkoxy;

(c) a thienyl group of the formula (4)

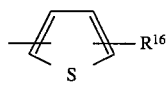

(4)

where $R^{16}$ is H, halo, halomethyl, CN, $NO_2$, $(C_1-C_4)$ alkyl, $(C_3-C_4)$ branched alkyl, phenyl, $(C_1-C_4)$ alkoxy, or thienyl;

(d) a group of formula (5) or (6)

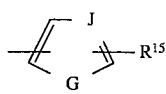

(5)

(6)

where $R^{15}$ is as defined in paragraph (b), J is N or CH, and G is O, $NR^{17}$, or S, provided that if J is not N then G is NR, where $R^{17}$ is H, $(C_1-C_4)$ alkyl, $(C_1-C_4)$ alkanoyl, phenylsulfonyl, or substituted phenylsulfonyl;

(e) a group selected from optionally substituted naphthyl, dihydronaphthyl, tetrahydronaphthyl, and decahydronaphthyl;

optionally substituted indolyl;

1,3-benzodioxolyl;

2,6-dimethyl-4-morpholinyl; and 1-adamantyl;

(f) a group of the formula

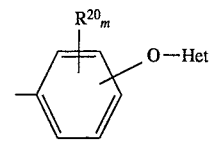

wherein m is 4; each $R^{20}$ is independently H, halo, lower alkyl, lower alkoxy, haloalkyl, haloalkoxy, $NO_2$, CN, lower alkyl carbonyl, $S(O)R^{14}$, $SO_2R^{14}$, or $OSO_2R^{14}$, phenoxy, or substituted phenoxy, where $R^{14}$ is $(C_1-C_{10})$ alkyl, phenyl, or substituted phenyl; provided that at least two of $R^{20}$ are selected from H and F; and Het is pyridinyl, pyrazinyl, pyrimidinyl, or pyridazinyl, optionally substituted with one or more groups selected from halo, lower alkyl, lower alkoxy, haloalkyl, haloalkoxy, $NO_2$, CN, and lower alkyl carbonyl;

(g) a group of the formula

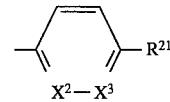

wherein one of $X^2$ and $X^3$ is N and the other is $CR^{23}$;

$R^{21}$ is $-T-R^{22}$, phenyl, substituted phenyl, $(C_1-C_{10})$ alkyl, halo, or halo $(C_1-C_8)$ alkyl, where T is O or S, and $R^{22}$ is $(C_1-C_4)$ alkyl, $(C_3-C_7)$ branched alkyl, halo $(C_1-C_7)$ alkyl, halo $(C_3-C_7)$ branched alkyl, $(C_1-C_4)$ alkoxy $(C_1-C_4)$ alkyl, or naphthyl or phenyl, either of which may be optionally substituted with up to three groups selected from halo, $(C_1-C_{10})$ alkyl, branched $(C_3-C_7)$ alkyl, halo $(C_1-C_7)$ alkyl, hydroxy $(C_1-C_7)$ alkyl, $(C_1-C_4)$ alkoxy, halo $(C_1-C_4)$ alkoxy, phenoxy, substituted phenoxy, phenyl, substituted phenyl, CN, $NO_2$, OH, $(C_1-C_4)$ alkanoyloxy, or benzyloxy;

$R^{23}$ is:

H, halo, $(C_3-C_8)$ cycloalkyl, $(C_3-C_8)$ cycloalkenyl, phenoxy, substituted phenoxy, phenylthio, substituted phenylthio, phenyl, substituted phenyl, $NO_2$,

where $R^8$ is $(C_1-C_7)$ alkyl, halo $(C_1-C_7)$ alkyl, $(C_3-C_7)$ branched alkyl, halo $(C_3-C_7)$ branched alkyl, $(C_3-C_7)$ cycloalkyl, halo $(C_3-C_7)$ cycloalkyl, $(C_1-C_7)$ alkoxy, phenyl, substituted phenyl, or hydroxy, acetoxy,

OH,

CN,

SiR$^9$R$^{10}$R$^{11}$ or OSiR$^9$R$^{10}$R$^{11}$, where R$^9$, R$^{10}$ and R$^{11}$ are independently (C$_1$–C$_4$) alkyl, (C$_3$–C$_4$) branched alkyl, phenyl, or substituted phenyl, NR$^{12}$R$^{13}$, where R$^{12}$ and R$^{13}$ are independently H, (C$_1$–C$_4$) alkyl, or (C$_1$–C$_4$) alkanoyl, S(O)R$^{14}$, or SO$_2$R$^{14}$, where R$^{14}$ is (C$_1$–C$_{10}$) alkyl, phenyl, or substituted phenyl;

a (C$_1$–C$_{12}$) saturated or unsaturated hydrocarbon chain, straight chain or branched optionally including a hetero atom selected from O, S, SO, SO$_2$, NR$^5$, or SiR$^6$R$^7$, where R$^5$, R$^6$ and R$^7$ are as defined above, and optionally substituted with halo, halo (C$_1$–C$_4$) alkoxy, hydroxy, (C$_3$–C$_8$) cycloalkyl or cycloalkenyl, (C$_1$–C$_4$) alkanoyl, phenoxy, substituted phenoxy, phenyl, substituted phenyl, phenylthio, substituted phenylthio, or cyano;

(C$_1$–C$_7$) alkoxy optionally substituted with halo, phenyl, substituted phenyl, (C$_3$–C$_8$) cycloalkyl or cycloalkenyl, phenoxy, or substituted phenoxy; or (C$_1$–C$_7$) alkylthio optionally substituted with halo, phenyl, substituted phenyl, (C$_3$–C$_8$) cycloalkyl or cycloalkenyl, phenoxy or substituted phenoxy; or Y-Z together form a (C$_2$–C$_{11}$) saturated or unsaturated hydrocarbon chain, straight chain or branched;

W is O, S(O)$_y$, wherein y is an integer from 0 to 2, or NR$^{24}$, where R$^{24}$ is H, OH, (C$_1$–C$_4$) alkyl, (C$_1$–C$_4$) alkoxy, aryl, (C$_1$–C$_4$) alkanoyl, NR$^{25}$R$^{26}$, benzyl, or benzyl optionally substituted with (C$_1$–C$_4$) alkyl, (C$_{1-C4}$) alkoxy, halo, halo (C$_1$–C$_4$) alkyl, and R$^{25}$ and R$^{26}$ are independently H, (C$_1$–C$_4$) alkyl, aryl, alkanoyl, or together form with nitrogen a saturated (C$_3$–C$_7$) ring such as morpholino, piperidinyl, pyrrolidinyl;

G is (C$_1$–C$_4$) alkyl, aryl, (C$_1$–C$_4$) alkanoyl, NR$^{25}$R$^{26}$, deuterio (C$_1$–C$_4$) alkyl, halo (C$_1$–C$_4$) alkyl, benzyl, or benzyl optionally substituted with (C$_1$–C$_4$) alkyl, (C$_1$–C$_4$) alkoxy, halo, or halo (C$_1$–C$_4$) alkyl, where R$^{25}$ and R$^{26}$ are as defined above; or W-G together are halo, SH, or NR$^{25}$R$^{26}$ where R$^{25}$ and R$^{26}$ are as defined above;

provided that the following compound is excluded:

(1) the compound of formula 1 wherein R$^1$ and R$^2$ are H, and Y-Z together form t-butyl.

The invention also provides a method of inhibiting a nematode population which comprises applying to the locus of a nematode, a nematode inactivating amount of a compound of the formula (1) or (2) as defined above.

The invention also provides a method of inhibiting an insect or mite population which comprises applying to the locus of the insect or arachnid an effective insect or mite inactivating amount of a compound of formula (1) or (2).

The invention also provides a method of inhibiting plant pathogens which comprises applying an effective amount of a compound of formula (1) or (2) to a locus of the pathogen.

Throughout this document, all temperatures are given in degrees Celcius, and all percentages are weight percentages unless otherwise stated.

The term "halo" refers to a F, Cl, Br, or I atom.

The terms "alkoxy", "haloalkyl", "alkylsulfinyl", and "alkylsulfonyl" refer to straight chain and branched chain groups.

The terms "substituted phenyl", "substituted phenoxy", "substituted phenylthio", and "substituted phenylsulfonyl", refer to such groups wherein the phenyl ring is substituted with up to three groups independently selected from halo, (C$_1$–C$_{10}$) alkyl, branched (C$_3$–C$_6$) alkyl, halo (C$_1$–C$_7$) alkyl, hydroxy (C$_1$–C$_7$) alkyl, (C$_1$–C$_7$) alkoxy, halo (C$_1$–C$_7$) alkoxy, phenoxy, substituted phenoxy, phenyl, substituted phenyl, NO$_2$, OH, CN, (C$_1$–C$_4$) alkanoyl, benzoyl, (C$_1$–C$_4$) alkanoyloxy, (C$_1$–C$_4$)alkoxycarbonyl, phenoxycarbonyl, or benzoyloxy, provided that a substituted phenyl, substituted phenyoxy, substituted phenylthio, or substituted phenylsulfonyl group that is itself substituted with a group from this list shall not include a total of more than three phenyl rings. Thus, for example, a phenyl group that is substituted in the 4-position with a 4-chlorophenoxy group is included in the definition of substituted phenyl.

The terms "substituted naphthyl", and "substituted indolyl" refer to these ring systems substituted with one or more groups independently selected from halo, halo (C$_1$–C$_4$) alkyl, CN, NO$_2$, (C$_1$–C$_4$) alkyl, (C$_3$–C$_4$) branched alkyl, phenyl, (C$_1$–C$_4$) alkoxy, or halo (C$_1$–C$_4$) alkoxy.

The term "carbocyclic ring" refers to a saturated or unsaturated carbocyclic ring containing five or six carbon atoms.

The term "unsaturated hydrocarbon chain" refers to a hydrocarbon chain containing one or more sites of unsaturation.

The term "HPLC" refers to a high pressure liquid chromatography.

The term "substituted amino" refers to an amino group that is substituted with one or two (C$_1$–C$_4$) alkyl groups or one (C$_1$–C$_4$) alkanoyl group.

The term "lower alkyl" refers to C1 to C6 straight hydrocarbon chains and C3 to C6 branched and cyclic hydrocarbon groups.

The terms "lower alkenyl" and "lower alkynyl" refer to C2 to C6 straight hydrocarbon chains and C3 to C6 branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

Unless otherwise indicated, when it is stated that a group may be substituted with one or more substituents selected from an identified class, it is intended that the substituents may be independently selected from the class.

Preferred compounds of formula (1) include the following classes:

a) compounds of formula (1) wherein Y is —CH$_2$—;

b) compounds of formulas (1) wherein Z is aryl;

c) compounds of formulas (1) wherein Z is a phenyl group substituted with a halo(C$_2$–C$_4$) alkoxy group;

d) compounds of formulas (1) wherein Z is a phenyl group substituted with a phenoxy or substituted phenoxy group;

e) compounds of any of the foregoing groups c) and d) wherein the phenyl group is monosubstituted in the 4-position;

f) compounds of the formula 1A

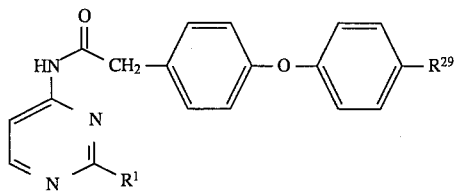

where $R^1$ is alkyl and $R^{29}$ is an electron withdrawing group, such as halo, halo($C_1$-$C_4$)alkyl; ($C_1$-$C_4$) alkanoyl, CN, $NO_2$, or $CF_3$.

Particularly preferred are Compounds of formula (1A) wherein $R^1$ is ethyl and $R^{29}$ is $CF_3$, CN, or Cl.

Synthesis

The compounds of this invention are made using well known chemical procedures. The required starting materials are commercially available, or they are readily synthesized using standard procedures.

Compounds of Formula (1) can be prepared using the process illustrated in the following schemes:

Scheme 1

Scheme 1

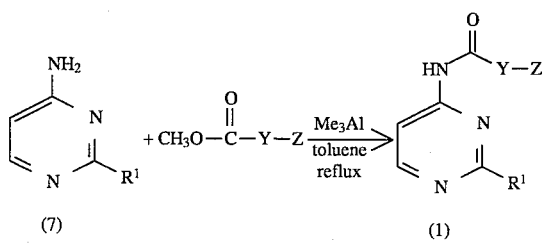

In the procedure illustrated in Scheme 1, the methylaluminum solution is added to a mixture of the aminopyrimidine (7) in toluene under nitrogen at room temperature. The solution is warmed and a solution of the ester in toluene is added. The resulting mixture is refluxed, then allowed to cool to room temperature and quenched by dropwise addition of 1M HCl. The mixture is then poured into 1N sodium hydroxide and extracted with a solution of diethyl ether/dichloromethane, dried over anhydrous sodium sulfate and concentrated.

Scheme 2

Scheme 2

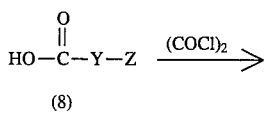

-continued
Scheme 2

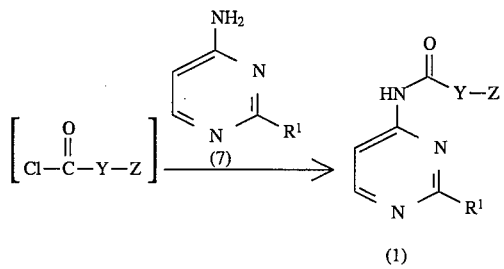

In the procedure illustrated in Scheme 2, a slight excess of oxalyl chloride is added dropwise to a solution of the carboxylic acid (8) in a suitable organic solvent, such as THF, methylene chloride, or xylenes, under nitrogen, at room temperature. The mixture may also include 1–2 equivalents of pyridine or triethylamine. After stirring the mixture for 30 minutes to 2 hours, the amine (7), in solution in a suitable organic solvent, such as THF, methylene chloride, or xylene, is added dropwise. The mixture is heated to reflux for 8 to 24 hours, then allowed to cool to room temperature and partitioned between 1N sodium hydroxide and ethyl ether. The aqueous phase is extracted with ethyl ether. The combined organics are washed with water and saturated sodium chloride solution, then dried, filtered, and concentrated.

Scheme 3

Scheme 3

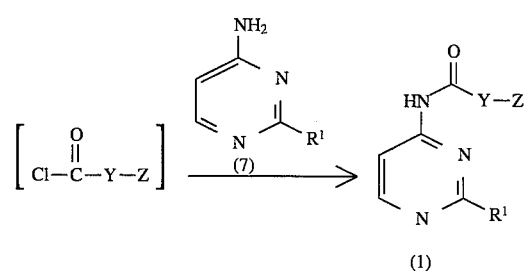

In the procedure illustrated in Scheme 3, an acid derivative (8) is heated to reflux in excess thionyl chloride for about two hours. The excess thionyl chloride is then removed by reducing pressure. To the residue is then added a solution of the amine (7), and optionally about two equivalents of triethylamine, in a suitable organic solvent, such as acetonitrile, toluene, or xylene. The mixture is heated to reflux for 8 to 24 hours, then allowed to cool to room temperature and partitioned between 1N sodium hydroxide and ethyl ether. The aqueous phase is extracted with ethyl ether. The combined organics are washed with water and saturated sodium chloride solution, then dried, filtered, and concentrated.

Compounds of formula

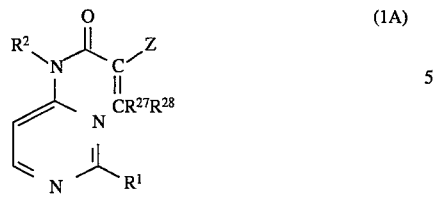
(1A)

can be prepared by using the processes illustrated in Scheme 4:

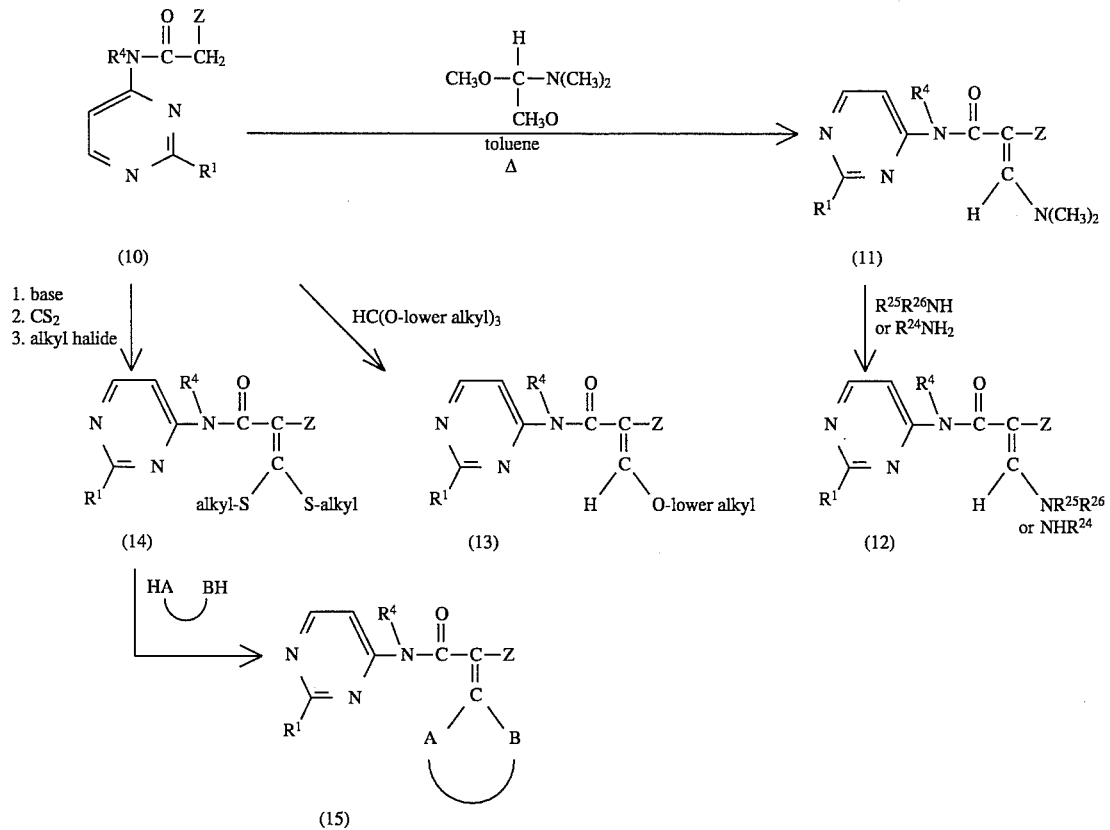

Methylene derivatives (11) wherein the methylene is substituted with $N(CH_3)_2$ may be prepared by treating the N-(4-pyrimidinyl)amide (10) with the appropriate N,N-dialkylcarboxamide di-alkylacetal in the presence of toluene with heating. The N,N-dialkyl derivatives (11) can be converted to their $NHR^{24}$ derivatives by treating with the appropriate amine to give (12). Treating the N-(4-pyrimidinyl)amides (10) with trialkyl-orthocarboxylates gives additional methylene derivatives (13). The N-(4-pyrimidinyl)amides (10) can also be converted to S,S-ketene acetals (14) and optionally, to cyclic systems (15).

Compounds of Formula (2) where W=O, S, or $NR^{24}$ can be prepared using the process illustrated in Scheme 5:

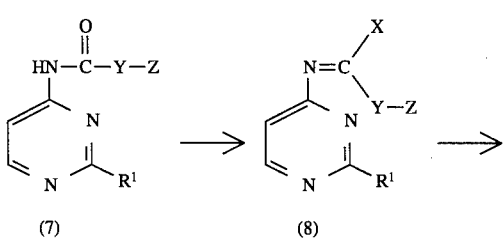

-continued
Scheme 5

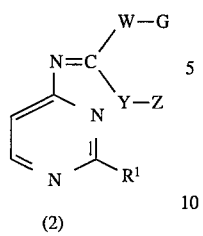

(2)

The carbonyl derivative (7) is converted to the corresponding imidoyl halide (8) by treatment with reagents such as PCl$_5$, PBr$_5$, POCl$_3$, POBr$_3$, oxalyl chloride, or SOCl$_2$. The imidoyl halide (8) can then be reacted with nucleophiles such as, for example, H$_2$S, OR$^-$, SR$^-$, NH$_2$R$^{24}$, NHR$^{25}$R$^{26}$, or NHR$^{24}$NR$^{25}$R$^{26}$ to give the desired compounds of Formula (2).

Compounds of Formula (2) where W-G is SH, or W is S and G is alkyl or benzyl can be prepared using the process illustrated in Scheme 6:

Scheme 6

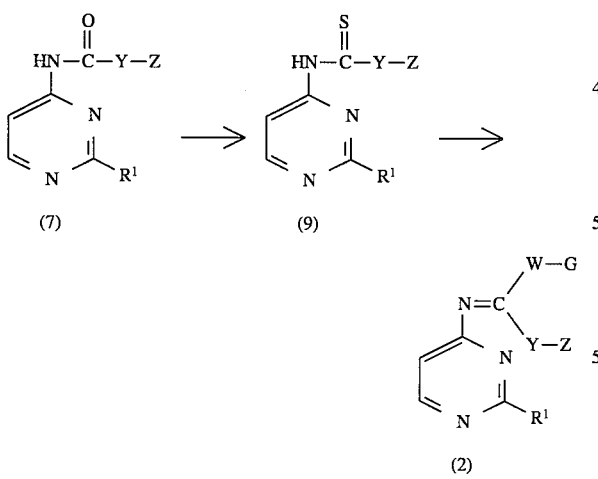

The carbonyl derivative (7) is treated with Lawesson's reagent or P$_2$S$_5$ to give the corresponding thione (9). The thione can then be alkylated with an alkyl halide or benzyl halide to give the desired compounds of Formula (2).

Starting Materials

Pyrimidin-4-amine starting materials of formula (7) can be prepared using the procedure illustrated in the following scheme 7:

Scheme 7

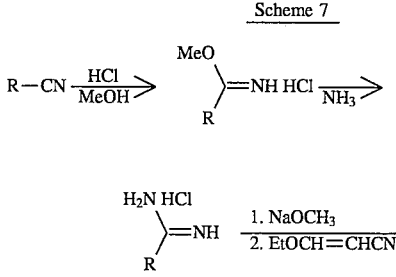

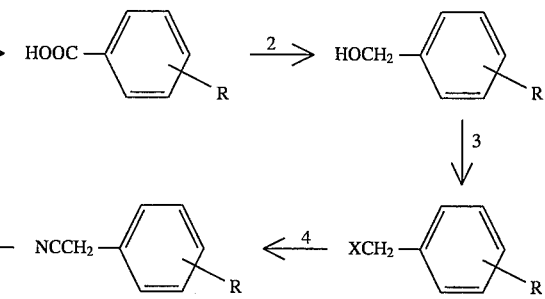

Carboxylic acids of formula (8) are also readily prepared using conventional procedures, for example the classic chain-lengthening procedure illustrated in the following scheme 8:

Scheme 8

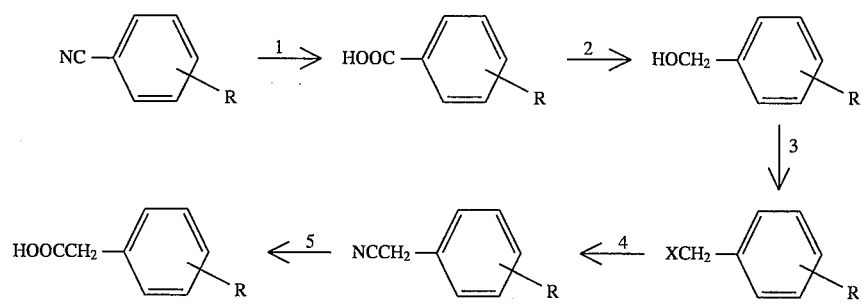

In step 1, KOH hydrolysis of the nitrile produces the corresponding carboxylic acid. In step 2, lithium aluminum hydride reduction of the carboxylic acid produces the alcohol. Alternatively, the alcohol can be obtained by sodium borohydride reduction of the corresponding aldehyde. The halogenation illustrated in step 3 may be, for example, chlorination with thionyl chloride. Treatment of the halide with NaCN in step 4 gives the nitrile. In step 5, hydrolysis of the nitrile gives the phenylacetic acid derivative.

Carboxylic acid derivatives of formula (8) wherein Z is a group of the formula

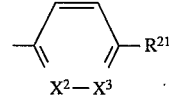

can be prepared using an analogous procedure. Carboxylic acid derivatives of formula (8) wherein Z is a group of the formula

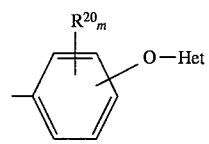

can be prepared by reacting p-hydroxyphenyl acetic acid with the appropriate chloro-substituted heterocyclic compound.

The N-oxides and salts of compounds of formula (1) are obtained in the usual way.

EXAMPLES

The following tables identify compounds of formula (1) that were prepared by the processes illustrated in the foregoing schemes. Detailed examples illustrating preparation of exemplary compounds follow the tables

TABLE I

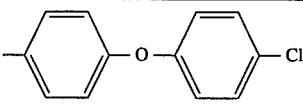

(1)

| Compound | Y | Z | R¹ | R² | MP °C. |
|---|---|---|---|---|---|
| 1 | $CH_2$ | 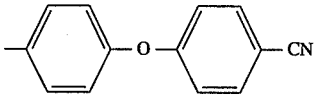 | $CH_3$ | H | 111–112 |
| 2 | $CH_2$ | 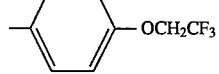 | $CH_3$ | H | 154 |
| 3 | $CH_2$ | 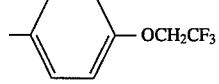 | $CH_3$ | H | 154–155 |
| 4 | $CH_2$ | 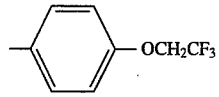 | $SCH_3$ | H | 124–126 |
| 5 | $CH_2$ | 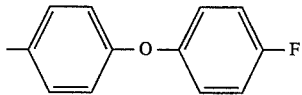 | Ph | H | 147–149 |
| 6 | $CH_2$ | 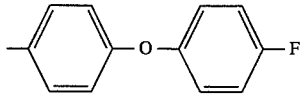 | $SCH_3$ | H | 130–132 |
| 7 | $CH_2$ | 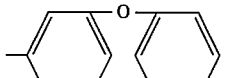 | Ph | H | 106–108 |
| 8 | $CH_2$ | 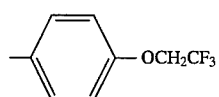 | $CH_3$ | H | oil |
| 9 | $CH_2$ | 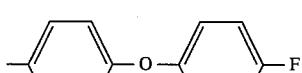 | Et | H | 82–84 |
| 10 | $CH_2$ | 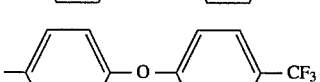 | Et | H | 84–86 |
| 11 | $CH_2$ |  | Et | H | wax |

TABLE I-continued $$\underset{R^2}{\overset{O}{\underset{N}{\|}}}\overset{}{\underset{}{}}Y-Z$$

(structure with pyrimidine ring bearing R¹ and N-C(=O)-Y-Z with R² on N) (1)

| Compound | Y | Z | R¹ | R² | MP °C. |
|---|---|---|---|---|---|
| 12 | CH₂ | –C₆H₄–O–C₆H₄–CN | Et | H | glass |
| 13 | CH₂ | –C₆H₄–O–(pyridyl)–CN | Et | H | 167–169 |
| 14 | CH₂ | –C₆H₄–O–(pyrimidinyl)–Br | Et | H | 193–194 |
| 15 | CH₂ | –C₆H₄–OCH₂CF₃ | c-Pr | H | 93–94 |
| 16 | CH₂ | –C₆H₄–O–C₆H₄–F | c-Pr | H | oil |
| 17 | CH₂ | –C₆H₄–O–C₆H₄–Cl | Et | H | 88–89 |
| 18 | CH₂ | –C₆H₄–OCH₂CF₃ | n-Pr | H | 106 |
| 19 | CH₂ | –C₆H₄–O–C₆H₄–F | n-Pr | H | 81–83 |
| 20 | CH₂ | –C₆H₄–OCH₂CF₃ | n-Bu | H | 92–94 |
| 21 | CH₂ | –C₆H₄–O–C₆H₄–F | n-Bu | H | 87–88 |
| 22 | CH₂ | –C₆H₄–OCH₂CF₃ | c-Bu | H | 105–106 |
| 23 | CH₂ | –C₆H₄–O–C₆H₄–F | c-Bu | H | 77–78 |

TABLE I-continued (1)

$$\underset{\substack{R^2\\|\\N\\\|\\N}}{\overset{O}{\underset{\|}{C}}}-Y-Z$$

(structure with $R^1$ on pyrimidine ring)

| Compound | Y | Z | $R^1$ | $R^2$ | MP °C. |
|---|---|---|---|---|---|
| 24 | $CH_2$ | 4-($OCH_2CF_3$)phenyl | t-Bu | H | 120–122 |
| 25 | $CH_2$ | 4-(4-F-phenoxy)phenyl | t-Bu | H | wax |
| 27 | $CH_2$ | 4-(4-F-phenoxy)phenyl | $CH_3$–C(=$CH_2$)– | H | 181–182 |
| 28 | $CH_2$ | 4-($OCH_2CF_3$)phenyl | H | H | 163 |
| 29 | $CH_2$ | 4-(4-Cl-phenoxy)phenyl | c-Pr | H | oil |
| 30 | $CH_2$ | 4-($OCH_2CF_3$)phenyl | i-Pr | H | 93–95 |
| 31 | $CH_2$ | 4-(4-F-phenoxy)phenyl | i-pr | H | 77–79 |
| 32 | $CH_2$ | 4-(3-F-5-$CF_3$-pyridin-2-yloxy)phenyl | Et | H | oil |
| 33 | $CH_2$ | $(CH_3)_2CH(CH_2)_4CH(n$-$C_3H_7)$- | Et | H | oil |
| 34* |  | n-$C_{17}H_{35}$ | Et | H | 82–83 |
| 35 | $CH_2$ | 6-methyl-3-($OCH_2CF_3$)pyridin-2-yl (aryl-pyridyl) | Et | H | 119–121 |
| 36 | $CH_2$ | 4-(5-$SO_2CH_3$-pyridin-2-yloxy)phenyl | Et | H | 61–62 |
| 37 | $CH_2$ | 4-(5-Cl-pyridin-2-yloxy)phenyl | Et | H | oil |
| 38 | $CH_2$ | 4-($OCH_2CF_3$)phenyl | $CH_2OCH_3$ | H | oil |

TABLE I-continued (1)

$$\text{structure with } R^2\text{-N(-C(=O)-Y-Z)-C=CH-CH=N-C(R^1)=N- ring}$$

| Compound | Y | Z | R¹ | R² | MP °C. |
|---|---|---|---|---|---|
| 39 | $CH_2$ | 4-(4-F-phenoxy)phenyl | $CH_2OCH_3$ | H | oil |
| 40 | $CH_2$ | biphenyl-4-yl | Et | H | 113–115 |
| 41 | $CH_2$ | 4-(n-butyl)phenyl (—C₆H₄—CH₂CH₂CH₂CH₃) | Et | H | 64–65 |
| 42 | $CH_2$ | 4-(OCHF₂)phenyl | Et | H | 64–66 |
| 43 | $CH_2$ | 4-(O—CH₂CF₂—CF₂H)phenyl | Et | H | oil |
| 44 | $CH_2$ | 4-(O—n-C₄H₉)phenyl | Et | H | 64–66 |
| 45 | $CH_2$ | 4-CH(CH₃)₂-phenyl | Et | H | oil |
| 46 | $CH_2$ | —O—(4-CH(CH₃)₂-phenyl) | Et | H | oil |
| 47 | $CH_2$ | 4-phenoxyphenyl | Et | H | oil |
| 48 | $CH_2$ | 4-(t-Bu)phenyl | Et | H | 87–89 |
| 49 | $CH_2$ | 4-(4-acetylphenoxy)phenyl | Et | H | oil |
| 50 | $CH_2$ | naphth-2-yl | Et | H | |

TABLE I-continued
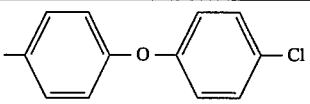
| Compound | Y | Z | R¹ | R² | MP °C. |
|---|---|---|---|---|---|
| 51 | $CH_2$ | —⟨⟩—O—⟨⟩—Cl | c-Pr | $CH_3$ | |
*Not a claimed compound
TABLE II
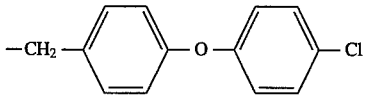
| Compound | Y | Y–Z | W–G | R¹ | MP °C. |
|---|---|---|---|---|---|
| 52 | $CH_2$ | —$CH_2$—⟨⟩—O—⟨⟩—Cl | O—$CH_3$ | c-Pr | oil |

TABLE III (1)

[Structure: Pyrimidine ring with N-C(=O)-Y-Z group, R² on nitrogen, R¹ on pyrimidine ring]

| Compound | Y | Z | R¹ | R² | MP °C. |
|---|---|---|---|---|---|
| 53 | $CH_2$ | –C₆H₄–O–C₆H₄–NO₂ | $C_2H_5$ | H | glass |
| 54 | $CH_2$ | –C₆H₄–O–C₆H₄–F | Cl | H | 154–156 |
| 55 | $CH_2$ | –C₆H₄–O–$CF_2CF_2H$ | $C_2H_5$ | H | 108–109 |
| 56 | $CH_2$ | –C₆H₄–O–$CH_2CF_3$ | $C_2H_5$ | $CH_3$ | |
| 57 | $CH_2$ | –C₆H₄–O–$CH_2CF_3$ | $C_2H_5$ | $C_2H_5$ | |
| 58 | $CH_2$ | –C₆H₄–O–C₆H₄–Cl | $C_2H_5$ | $CH_3$ | |
| 59 | $CH_2$ | –C₆H₄–O–C₆H₄–Cl | t-Bu | H | 121–122 |
| 60 | $CH_2$ | –C₆H₄–O–C₆H₄–CN | t-Bu | H | 67–68 |
| 61 | $CH_2$ | –C₆H₄–O–C₆H₄–Cl | $C_2H_5$ | $C_2H_5$ | |
| 62 | $CH_2$ | –C₆H₄–O–C₆H₄–$CF_3$ | t-Bu | H | 108–111 |
| 63 | $CH_2$ | –C₆H₄–O–C₆H₄–$CF_3$ | $CH_3$ | H | 110–112 |
| 64 | $CH_2$ | –C₆H₄–O–$CF_2CF_2H$ | $C_2H_5$ | $CH_3$ | |
| 65 | $CH_2$ | –C₆H₄–O–C₆H₄–$CF_3$ | n-Bu | H | 68–72 |

TABLE III-continued

Structure (1):

R²\N(–C(=O)–Y–Z) attached to a pyrimidine ring with R¹ substituent

| Compound | Y | Z | R¹ | R² | MP °C. |
|---|---|---|---|---|---|
| 66 | CH₂ | –C₆H₄–O–C₆H₄–CF₃ (4,4') | c-Bu | H | 64–69 |
| 67 | CH₂ | –C₆H₄–O–C₆H₄–CF₃ (4,4') | c-Pr | H | <72 |
| 68 | CH₂ | –C₆H₄–O–C₆H₄–CF₃ (4,4') | H | H | |
| 69 | CH₂ | –C₆H₄–O–C₆H₄–CF₃ (4,3') | CH₃ | H | 80–84 |
| 70 | CH₂ | –C₆H₄–O–C₆H₄–CF₃ (4,4') | CH₂OCH₃ | H | |
| 71 | CH₂ | –C₆H₄–O–C₆H₄–CF₃ (4,3') | c-Bu | H | |
| 72 | CH₂ | –C₆H₄–O–C₆H₄–CF₃ (4,4') | i-Pr | H | oil |

TABLE IV

Structure (12A)

| Compound | R²⁵ | R²⁶ | Z | MP °C. |
|---|---|---|---|---|
| 73 | CH₃ | CH₃ | –C₆H₄–O–C₆H₄–CF₃ | |

TABLE IV-continued (12A)

[Structure shown: pyrimidine ring with C₂H₅ substituent, connected via HC=N-NR²⁵R²⁶ and HN-C(=O)-Z groups]

| Compound | R²⁵ | R²⁶ | Z | MP °C. |
|---|---|---|---|---|
| 74 | CH₃ | CH₃ | —C₆H₄—OCF₂CF₂H | oil |
| 75 | H | C₂H₅ | —C₆H₄—OCF₂CF₂H | oil |
| 76 | CH₃ | CH₃ | —C₆H₄—O—C₆H₄—Cl | |
| 77 | H | C₂H₅ | —C₆H₄—O—C₆H₄—Cl | |
| 78 | CH₃ | CH₃ | —C₆H₄—O—C₆H₄—CN | 80–82 |
| 79 | H | C₂H₅ | —C₆H₄—O—C₆H₄—CN | |
| 80 | H | CH₂CH(CH₃)₂ | —C₆H₄—O—C₆H₄—CN | oil |

As will be apparent to those of ordinary skill in the art, the compounds identified by structure in the foregoing Tables have the following chemical names:

1) 4-(4-chlorophenoxy)phenyl-N-(2-methyl-4-pyrimidinyl)acetamide;
2) 4-(4-cyanophenoxy)phenyl-N-(2-methyl-4-pyrimidinyl)acetamide;
3) 4-(2,2,2-trifluroethoxy)phenyl -N-(2-methyl-4-pyrimidinyl)acetamide;
4) 4-(2,2,2-trifluroethoxy)phenyl-N-(2-methylthio- 4-pyrimidinyl)acetamide;
5) 4-(2,2,2-trifluroethoxy)phenyl-N-(2-phenyl-4-pyrimidinyl)acetamide;
6) 4-(4-fluorophenoxy)phenyl-N-(2-methylthio-4-pyrimidinyl)acetamide;
7) 4-(4-fluorophenoxy)phenyl-N-(2-phenyl-4-pyrimidinyl)acetamide;
8) 3-phenoxyphenyl-N-(2-methyl-4-pyrimidinyl)acetamide;
9) 4-(2,2,2-trifluroethoxy)phenyl-N-(2-ethyl-4-pyrimidinyl)acetamide;
10) 4-(4-fluorophenoxy)phenyl-N-(2-ethyl-4-pyrimidinyl)acetamide;
11) 4-(4-trifluoromethylphenoxy)phenyl-N-(2-ethyl-4-pyrimidinyl)acetamide;
12) 4-(4-cyanophenoxy)phenyl-N-(2-ethyl-4-pyrimidinyl)acetamide;
13) 4-(5-cyano-2-pyridinyloxy)phenyl-N-(2-ethyl-4-pyrimidinyl)acetamide;
14) 4-(5-bromo-2-pyrimidinyloxy)phenyl-N-(2-ethyl-4-pyrimidinyl)acetamide;
15) 4-(2,2,2-trifluroethoxy)phenyl-N-(2-cyclopropyl-4-pyrimidinyl)acetamide;
16) 4-(4-fluorophenoxy)phenyl-N-(2-cyclopropyl-4-pyrimidinyl)acetamide;
17) 4-(4-chlorophenoxy)phenyl-N-(2-ethyl-4-pyrimidinyl)acetamide;
18) 4-(2,2,2-trifluroethoxy)phenyl-N-(2-propyl-4-pyrimidinyl)acetamide;
19) 4-(4-fluorophenoxy)phenyl-N-(2-propyl-4-pyrimidinyl)acetamide;
20) 4-(2,2,2-trifluroethoxy)phenyl-N-(2-butyl-4-pyrimidinyl)acetamide;
21) 4-(4-fluorophenoxy)phenyl-N-(2-butyl-4-pyrimidinyl)acetamide;
22) 4-(2,2,2-trifluroethoxy)phenyl-N-(2-cyclobutyl-4-pyrimidinyl)acetamide;
23) 4-(4-fluorophenoxy)phenyl-N-(2-cyclobutyl-4-pyrimidinyl)acetamide;

24) 4-(2,2,2-trifluroethoxy)phenyl-N-(2-(1,1-dimethylethyl)-4-pyrimidinyl)acetamide;
25) 4-(4-fluorophenoxy)phenyl-N-(2-(1,1-dimethylethyl)-4-pyrimidinyl)acetamide;
27) 4-(4-fluorophenoxy)phenyl-N-(2-(1-methylethenyl)-4-pyrimidinyl)acetamide;
28) 4-(2,2,2-trifluroethoxy)phenyl-N-(4-pyrimidinyl)acetamide;
29) 4-(4-chlorophenoxy)phenyl-N-(2-cyclopropyl-4-pyrimidinyl)acetamide;
30) 4-(2,2,2-trifluroethoxy)phenyl-N-(2-(1-methylethyl)-4-pyrimidinyl)acetamide;
31) 4-(4-fluorophenoxy)phenyl-N-(2-(1-methylethyl)-4-pyrimidinyl)acetamide;
32) 4-(3-fluoro-5-trifluromethyl-2-pyridinyloxy)phenyl-N-(2-ethyl-4-pyrimidinyl)acetamide;
33) N-(2-ethyl-4-pyrimidinyl)-2 methyldecamide;
35) 5-(2,2,2-trifluoromethoxy)-2-pyridinyl-N-(2-ethyl-4-pyrimidinyl)acetamide;
36) 4-(5-methylsulfonyl-2-pyridinyloxy)phenyl-N-(2-ethyl-4-pyrimidinyl)acetamide;
37) 4-(5-chloro-2-pyridinyloxy)phenyl-N-(2-ethyl-4-pyrimidinyl)acetamide;
38) 4-(2,2,2-trifluroethoxy)phenyl-N-(2-(methoxymethyl)-4-pyrimidinyl)acetamide;
39) 4-(4-fluorophenoxy)phenyl-N-(2-(methoxymethyl)-4-pyrimidinyl)acetamide;
40) biphenyl-N-(2-ethyl-4-pyrimidinyl)acetamide;
41) 4-pentylphenyl-N-(2-ethyl-4-pyrimidinyl)acetamide;
42) 4-difluromethoxy-N-(2-ethyl-4-pyrimidinyl)acetamide;
43) 4-(2,2,3,3-tetrafluropropoxy)phenyl-N-(2-ethyl-4-pyrimidinyl)acetamide;
44) 4-butoxyphenyl-N-(2-ethyl-4-pyrimidinyl)acetamide;
45) 4-(1-methylethyl)phenyl-N-(2-ethyl-4-pyrimidinyl)acetamide;
46) 4-(1-methylethyl)phenoxy-N-(2-ethyl-4-pyrimidinyl)acetamide;
47) 4-phenoxyphenyl-N-(2-ethyl-4-pyrimidinyl)acetamide;
48) 4-(1,1-dimethylethyl)phenyl-N-(2-ethyl-4-pyrimidinyl)acetamide;
49) 4-(4-acetylphenoxy)phenyl-N-(2-ethyl-4-pyrimidinyl)acetamide;
50) 2-naphthyl-N-(2-ethyl-4-pyrimidinyl)acetamide;
51) 4-(4-chlorophenoxy)phenyl-N-cyclopropyl-N-methylacetamide;
53) 4-(4-nitrophenoxy)phenyl-N-(2-ethyl-4-pyrimidinyl)acetamide;
54) 4-(4-fluorophenoxy)phenyl-N-(2-chloro-4-pyrimidinyl)acetamide;
55) 4-(1,1,2,2-tetrafluoroethoxy)phenyl-N-(2-ethyl-4-pyrimidinyl)acetamide;
56) 4-(2,2,2-trifluoroethoxy)phenyl-N-(2-ethyl-4-pyrimidinyl)-N-methylacetamide;
57) 4-(2,2,2-trifluoroethoxy)phenyl-N-ethyl-N-(2-ethyl-4-pyrimidinyl)acetamide;
58) 4-(4-chlorophenoxy)phenyl-N-methyl-N-(2-ethyl-4-pyrimidinyl)acetamide;
59) 4-(4-chlorophenoxy)phenyl-N-(2-(1,1-dimethylethyl)-4-pyrimidinyl)acetamide;
60) 4-(4-cyanophenoxy)phenyl-N-(2-(1,1-dimethylethyl)-4-pyrimidinyl)acetamide;
61) 4-(4-chlorophenoxy)phenyl-N-ethyl-N-(2-ethyl-4-pyrimidinyl)acetamide;
62) 4-(4-trifluoromethylphenoxy)phenyl-N-(2-(1,1-dimethylethyl)-4-pyrimidinyl)acetamide;
63) 4-(4-trifluoromethylphenoxy)phenyl-N-(2-methyl-4-pyrimidinyl)acetamide;
64) 4-(1,1,2,2-tetrafluoroethoxy)phenyl-N-(2-ethyl-4-pyrimidinyl)-N-methylacetamide;
65) 4-(4-trifluoromethylphenoxy)phenyl-N-(2-butyl-4-pyrimidinyl)acetamide;
66) 4-(4-trifluoromethylphenoxy)phenyl-N-(2-cyclobutyl-4-pyrimidinyl)acetamide;
67) 4-(4-trifluoromethylphenoxy)phenyl-N-(2-cyclopropyl-4-pyrimidinyl)acetamide;
68) 4-(4-trifluoromethylphenoxy)phenyl-N-(4-pyrimidinyl)acetamide;
69) 4-(3-trifluoromethylphenoxy)phenyl-N-(2-methyl-4-pyrimidinyl)acetamide;
70) 4-(4-trifluoromethylphenoxy)phenyl-N-(2-(methoxymethyl)-4-pyrimidinyl)acetamide;
71) 4-(3-trifluoromethylphenoxy)phenyl-N-(2-cyclobutyl-4-pyrimidinyl)acetamide;
72) 4-(4-trifluoromethylphenoxy)phenyl-N-(2-(1-methylethyl)-4-pyrimidinyl)acetamide;
73) 3-(dimethylamino)-N-(2-ethyl-4-pyrimidinyl)-1-(4-(4-trifluoromethylphenoxy)phenyl)-2-propenamide;
74) 3-(dimethylamino)-N-(2-ethyl-4-pyrimidinyl)-1-(4-(1,1,2,2-tetrafluoromethoxy)phenyl)-2-propenamide;
75) 3-(ethylamino)-N-(2-ethyl-4-pyrimidinyl)-1-(4-(1,1,2,2-tetrafluoromethoxy)phenyl)-2-propenamide;
76) 3-(dimethylamino)-N-(2-ethyl-4-pyrimidinyl)-1-(4-(4-chlorophenoxy)phenyl)-2-propenamide;
77) 3-(ethylamino)-N-(2-ethyl-4-pyrimidinyl)-1-(4-(4-chlorophenoxy)phenyl)-2-propenamide;
78) 3-(dimethylamino)-N-(2-ethyl-4-pyrimidinyl)-1-(4-(4-cyanophenoxy)phenyl)-2-propenamide;
79) 3-(ethylamino)-N-(2-ethyl-4-pyrimidinyl)-1-(4-(4-cyanophenoxy)phenyl)-2-propenamide;
80) 3-(2-methylpropylamino)-N-(2-ethyl-4-pyrimidinyl)-2-(4-(4-cyanophenoxy)phenyl)-2-propenamide.

Example 1

(Compound 1)

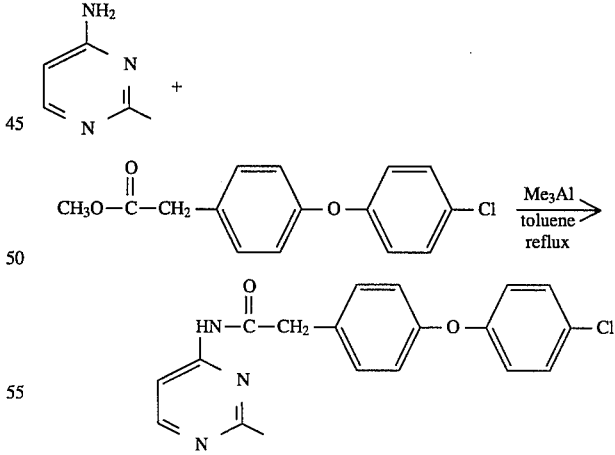

A 2.0M solution of trimethylaluminum in hexane (2.0 mL, 4.0 mmoL) was added dropwise to a mixture of 4-amino-2-methylpyrimidine (0.394 g, 3.6 mmoL) in 15 mL of toluene, under a nitrogen atmosphere, at room temperature. The resultant mixture was stirred at room temperature for 15 minutes, warmed slightly with a heat gun, treated with a solution of the ester in 2 mL of toluene and then heated to reflux. After refluxing overnight (17 h), the reaction mixture was allowed to cool to room temperature, quenched by the cautious, dropwise addition of 8 mL of 1M HCl, poured into 1N sodium hydroxide (75 mL) and extracted with a 2:1 solution of diethyl ether/dichloromethane (3×100 mL). The combined organic extracts were washed with water (1×100 mL), saturated sodium chloride (1×100 mL), dried over anhydrous sodium sulfate and concentrated under reduced pressure to give 1.12 g of a yellow oil. The crude product was purified by chromatography on silica gel (mplc) eluting with 70% hexane/30% ethyl acetate. This gave 0.583 g of the product as a white solid (46% yield).

Example 2

(Compound 4)

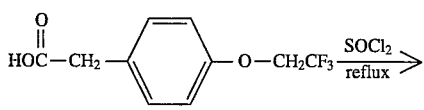

A solution of the phenylacetic acid (1.288 g, 5.5 mmoL) and excess thionyl chloride (10 mL) was refluxed for sixty minutes. The excess thionyl chloride was removed under reduced pressure. The acid chloride was taken up in dichloromethane and then concentrated to remove any residual thionyl chloride (two times). The acid chloride was then treated with a solution of 4-amino-2methylthiopyrimidine (0.706 g, 5.0 mmoL) in 10 mL of toluene and the resultant mixture was heated to reflux. After refluxing overnight (16 h), the reaction mixture was allowed to cool to room temperature, poured into 1N sodium hydroxide (75 mL) and then extracted with a 2:1 solution of diethyl ether/dichloromethane (3×100 mL). The combined organic extracts were washed with water (1×100 mL), saturated sodium chloride (1×100 mL), dried over anhydrous sodium sulfate and then concentrated under reduced pressure to give 2.20 g of a yellow solid. The crude product was purified by chromatographing on silica gel (mplc), eluting with 75% hexane/25% ethyl acetate. This gave 1.583 g of the product as a yellow solid (89% yield).

Example 3

(Compound 13)

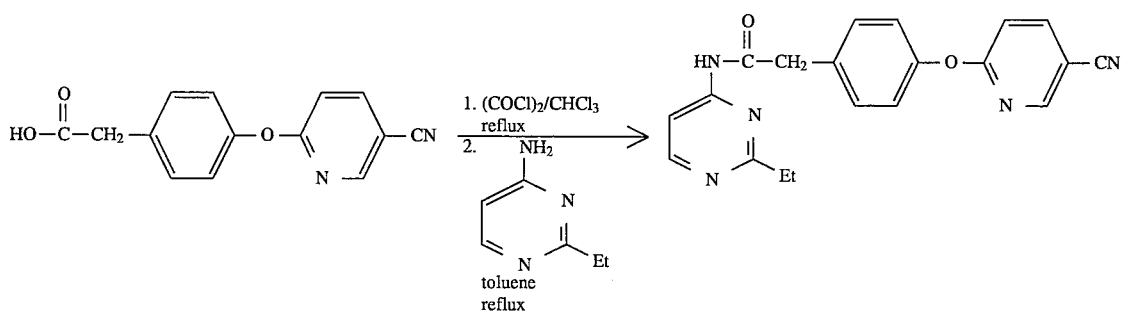

-continued
(Compound 4)

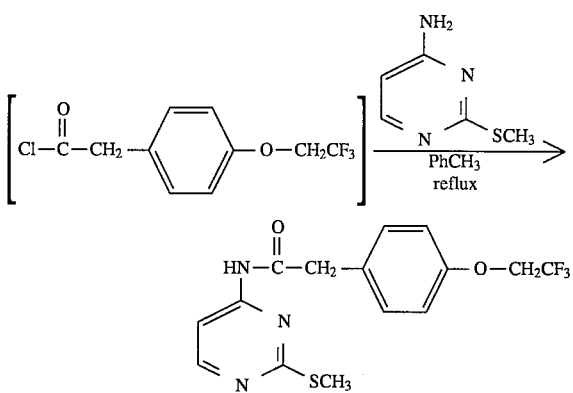

A solution of the phenylacetic acid (1.398 g, 5.5 mmoL) in 10 mL of chloroform was treated with an excess of oxalyl chloride (5 mL) and the resultant mixture was heated to reflux. After refluxing for sixty minutes, the reaction mixture was concentrated under reduced pressure. The acid chloride was taken up in chloroform and concentrated again. A solution of the acid chloride in 10 mL of toluene was treated in one portion with 4-amino-2-ethylpyrimidine and the resultant mixture was heated to reflux. After refluxing overnight (17 h), the reaction mixture was allowed to cool to room temperature, poured into 1N sodium hydroxide (100 mL) and extracted with a 2:1 solution of diethyl ether/dichloromethane (3×100 mL). The combined organic extracts were washed with water (1×100 mL), saturated sodium chloride (1×100 mL), dried over anhydrous sodium sulfate and then concentrated under reduced pressure to give 1.65 g of a brown oil. The crude product was purified by chromatographing on silica gel (mplc), eluting with 70% hexane/30% ethyl acetate. This gave 0.819 g of the product as a yellow solid (46% yield).

Example 4

(Compound 52)

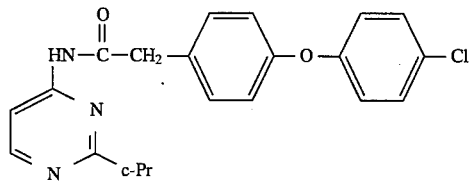 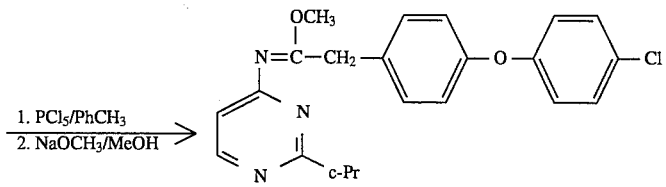

1. PCl$_5$/PhCH$_3$
2. NaOCH$_3$/MeOH

Phosphorus pentachloride was added to a solution of the amide in 10 mL of toluene and the resultant mixture was warmed to 45° C. After stirring at 45°–50° C. for 60 minutes, the mixture was concentrated in vacuo. A solution of the imidoyl chloride in 5 mL of methanol was added to solution of sodium methoxide in 5 mL of methanol and the resultant mixture was heated to reflux. After refluxing about 18 hours the mixture was poured into 50 mL of water, brought to a pH of 5–6 with 1M HCl, and extracted with methylene chloride (2×50 mL) and ethyl acetate (1×50 mL). The combined organics were washed with saturated sodium chloride solution (1×50 mL), dried (sodium sulfate), filtered, and concentrated to give 0.57 g of a yellow oil, which was purified on a preparative HPLC (C$_{18}$ column), eluting with 90% CH$_3$CN/10% H$_2$O. This gave 63 mg of the product as a colorless oil.

Insecticide and Miticide Utility

The compounds of formulas (1) and (2) show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against lo greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

The compounds of formulas (1) and (2) are useful for reducing populations of insects and mites, and are used in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant pats, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

Some of the above identified compounds were tested for insecticidal, miticidal and nematicidal activity against eight species. Results are reported in the following table, wherein the following abbreviations are used:

ALH refers to aster leafhopper
BAW refers to beet armyworm
CA refers to cotton aphid
NEM refers to peanut rootknot nematode
SCRW refers to southern corn rootworm
TBW refers to tobacco budworm
TSSM refers to two spotted spider mite
GECR refers to German cockroach In conducting evaluations of insecticidal activity, each test compound was formulated as a 400 ppm solution, and this solution was then diluted with water to give lesser concentrations. The 400 ppm solution was prepared by combining 19.2 mL of 0.05% solution of Tween 20 (polyoxyethylene (20) sorbitan monolaurate) in water with a solution of 8 mg of the compound in 0.8 mL of acetone/ EtOH (9/1).

Activity against aster leafhopper (*Macrosteles fascifrons*) was tested as follows. The test was run using concentrations of 400 ppm and 50 ppm. One ounce plastic cups containing a cotton wick was sprayed with 0.4 mL of formulated material using a flat-fan nozzle. The excess moisture was allowed to evaporate. Then five to ten carbon dioxide anesthetized adult leafhoppers were added to each cup. The cups were capped and held at room temperature for 24 hours. Percent mortality was then determined.

Activity against beet armyworm (*Spodoptera exiqua*) was evaluated as follows. The test is run using concentrations of 400 ppm and 50 ppm. A general purpose lepidoptera artificial diet was diluted to half strength with a 5% non nutritive agar. 8 mL of this diet material was dispensed into one ounce diet cups. One hour prior to treatment, 35 to 40 eggs were dispensed onto the diet surface. The cups were then sprayed with formulated material through a flat-fan nozzle. Treated cups were air dried prior to sealing with plastic caps. The cups were held for 6 days at room temperature. Activity was then rated based on the total number of live and dead larvae, and on the size of live larvae. Activity against cotton aphid (*Aphis gossypii*) and two spotted spider mite (*Tetranychus urticae*) was evaluated as follows. Golden crookneck squash plants were grown to the expanded cotyledon stage (about 6 to 8 days). The plants were infested with cotton aphids and two spotted spider mites 16 to 24 hours before application of the test material by transfer of infested foliage cut from a stock colony. Immediately prior to spray application of the test material the transfer foliage is removed from the squash plants. The test is run using concentrations of 400 ppm and 50 ppm. The plants are sprayed with test solution using an atomizing sprayer at 17 psi. Both surfaces of the leaves are covered until runoff, and then allowed to dry. Activity of each compound was determined three days after treatment. Activity was rated as a percent based on the mites/aphids present in plants sprayed with solvent alone.

Activity against peanut root knot nematode (*Meloidogyne arenaria*) was evaluated as follows. Five untreated cucumber seeds are placed into the bottom of a clear one ounce cup, 20 g of clean white sand is added, and the cups were sprayed while rotating on a pedestal allowing 1.0 mL of a 400 ppm solution to be deposited on the sand. To each cup was dispensed 2.5 to 3.0 mL of deionized water containing 300 to 500 nematodes. The cups were held for 10 to 12 days in an environmental growth chamber at a temperature of 76° to 85° F. and ambient humidity of 50 to 60%. After 10 to 12 days the cups were evaluated by inverting the cup and observing nematode mortality and feeding damage to the cucumber plants.

Activity on Southern corn rootworm (*Diabrotica undecimpuctata howardi* Barber) was evaluated by adding one mL of test solution containing a predetermined concentration of test compound to a cup containing a kernel of corn in 16 g of sterile soil. This produces a soil concentration of 24 ppm.

After 1.5 to 2 hours of drying, five 4th instar corn rootworm larvae were added to the individual cups. Mortality was measured at 3–4 days by emptying the cup onto a pan and inspecting the soil for live rootworms.

Activity against tobacco budworm (*Heliothis virescens*) was evaluated as follows. A general purpose lepidoptera artificial diet was diluted to half strength with a 5% non nutritive agar. 8 mL of this diet material was dispensed into each one ounce diet cup. One hour prior to treatment 18 to 20 eggs were dispensed onto the diet surface. The cups were then sprayed with formulated material through a flat-fan nozzle. The test was run using concentrations of 400 ppm and 50 ppm. Treated cups were air dried prior to sealing with plastic caps. The cups were held for 6 days at room temperature. Activity was then rated based on the total number of live and dead larvae, and on the size of live larvae.

Activity against German cockroach (*Blattella germanicus*) was evaluated as follows. 8 mL of alfalfa based green insect diet material was dispensed into a one ounce diet cup. The cups were then sprayed with formulated material through a flat-fan nozzle. The test was run using concentrations of 400 ppm and 50 ppm. Treated cups were air dried for 24 hours and infested with five late third or early fourth instar German cockroaches. The cups were capped and held for ten days in an environmental growth chamber at a temperature of 76°–85° C. Activity was then rated based on the total number of live and dead insects.

| INSECTICIDE, MITICIDE, AND NEMATICIDE DATA (percent mortality) | | | | | | | | |
|---|---|---|---|---|---|---|---|---|
| Compound | ALH 400 ppm | BAW 400 ppm | CA 400 ppm | RKN 400 ppm | SCRW 400 ppm | TBW 400 ppm | TSSM 400 ppm | GECR 400 ppm |
| 1 | 0 | 100 | 100 | 100 | 100 | 100 | 100 | 100 |
| 5 | 0 | 30 | 0 | 0 | 0 | 0 | 0 | 0 |
| 6 | 100 | 100 | 100 | 0 | 100 | 90 | 0 | 60 |
| 7 | 0 | 60 | 100 | 0 | 0 | 60 | 0 | 60 |
| 8 | 100 | 0 | 100 | 0 | 0 | 0 | 0 | 40 |
| 9 | 100 | 100 | 100 | 0 | 0 | 100 | 0 | 0 |
| 10 | 100 | 100 | 100 | 90 | 100 | 100 | 100 | 100 |
| 11 | 80 | 100 | 100 | 80 | 100 | 100 | 100 | 100 |
| 12 | 100 | 100 | 100 | 100 | 100 | 100 | 100 | 100 |
| 13 | 0 | 100 | 100 | 100 | 0 | 100 | 100 | 60 |
| 14 | 100 | 100 | 100 | 0 | 0 | 80 | 0 | 0 |
| 17 | | 100 | 100 | 100 | 100 | 100 | 100 | 100 |
| 18 | | 100 | 100 | 100 | 0 | 80 | 80 | 20 |
| 19 | | 100 | 100 | 100 | 100 | 100 | 100 | 100 |
| 20 | | 100 | 0 | 80 | 100 | 0 | 0 | 0 |
| 21 | | 100 | 100 | 90 | 0 | 100 | 100 | 100 |
| 22 | | 100 | 100 | 100 | 100 | 0 | 100 | 80 |
| 23 | | 100 | 100 | 100 | 0 | 100 | 100 | 100 |
| 24 | | 100 | 90 | 0 | 100 | 100 | 60 | 0 |
| 25 | | 100 | 100 | 100 | 100 | 100 | 100 | 100 |
| 27 | | 0 | 100 | 0 | 0 | 0 | 0 | 0 |
| 28 | | 0 | 100 | 0 | 0 | 0 | 0 | 0 |
| 29 | | 100 | 100 | 0 | 0 | 100 | 100 | 100 |
| 30 | | 100 | 100 | 100 | 100 | 90 | 100 | 80 |
| 31 | | 100 | 100 | 0 | 0 | 100 | 100 | 100 |
| 32 | | 100 | 100 | 100 | 0 | 100 | 100 | 60 |
| 33 | | 0 | 80 | 0 | 0 | 0 | 40 | 20 |
| 34 | | 0 | 0 | 0 | 0 | 0 | 0 | 20 |
| 35 | | 100 | 100 | 100 | 100 | 60 | 100 | 80 |
| 36 | | 100 | 40 | 100 | 0 | 100 | 0 | 40 |
| 37 | | 100 | 0 | 0 | 0 | 100 | 0 | 100 |
| 38 | | 0 | 0 | 0 | 0 | 0 | 0 | 0 |
| 39 | | 100 | 100 | 100 | 0 | 100 | 100 | 100 |
| 40 | | 20 | 60 | | | 40 | 0 | |
| 41 | | 100 | 100 | | | 40 | 100 | |
| 42 | | 40 | 100 | | | 0 | 100 | |
| 43 | | 60 | 100 | | | 60 | 100 | |
| 44 | | 100 | 100 | | | 0 | 90 | |

INSECTICIDE, MITICIDE, AND NEMATICIDE DATA
(percent mortality)

| Compound | ALH 400 ppm | BAW 400 ppm | CA 400 ppm | RKN 400 ppm | SCRW 400 ppm | TBW 400 ppm | TSSM 400 ppm | GECR 400 ppm |
|---|---|---|---|---|---|---|---|---|
| 45 |  | 100 | 100 |  |  | 0 | 100 |  |
| 46 |  | 0 | 0 |  |  | 0 | 0 |  |
| 47 |  | 100 | 100 |  |  | 40 | 100 |  |
| 48 |  | 0 | 100 |  |  | 20 | 100 |  |
| 49 |  | 100 | 100 |  |  | 40 | 100 |  |
| 50 |  | 60 | 100 |  |  | 40 | 100 |  |
| 53 | 90 | 100 | 100 | 100 | 100 | 100 | 100 | 80 |
| 54 | 0 | 100 | 0 | 0 | 0 | 60 | 0 | 0 |
| 55 | 100 | 100 | 100 | 100 | 100 | 80 | 100 | 100 |
| 59 | 80 | 100 | 100 | 0 | 100 | 100 | 0 | 100 |
| 60 | 100 | 100 | 100 | 100 | 100 | 100 | 100 | 100 |
| 62 | 80 | 100 | 100 | 0 | 100 | 100 | 100 | 100 |
| 63 | 60 | 100 | 100 | 0 | 0 | 100 | 100 | 100 |
| 65 | 0 | 100 | 100 |  | 0 | 100 | 100 | 100 |
| 66 | 40 | 100 | 100 |  | 100 | 100 | 100 | 100 |
| 67 | 60 | 100 | 100 | 100 | 100 | 100 | 100 | 100 |
| 68 | 0 | 0 | 0 | 100 | 0 | 100 | 0 | 0 |
| 69 | 40 | 80 | 0 |  | 0 | 80 | 0 | 0 |
| 70 | 0 | 100 | 90 | 0 | 0 | 60 | 80 | 100 |
| 71 | 0 | 100 | 0 | 0 | 0 | 60 | 0 | 100 |
| 72 |  | 0 | 100 | 100 | 100 | 100 | 100 | 100 |
| 73 | 100 | 100 | 100 | 100 | 100 | 100 | 100 | 100 |
| 76 | 100 | 100 | 100 | 100 | 100 | 100 | 80 | 80 |
| 78 | 60 | 100 | 80 | 100 | 0 | 100 | 80 | 80 |
| 79 | 80 | 100 | 100 | 100 | 100 | 100 | 100 | 100 |
| 80 | 60 | 100 | 100 | 100 | 100 | 100 | 100 | 100 |

Nematicide Utility

The compounds of the present invention are useful for reducing populations of nematodes. Accordingly, a significant aspect of the invention is a method of inhibiting a nematode population which comprises applying to a locus of a nematode an effective nematode inactivating amount of a compound of formula (1) or (2). The term "inhibiting a nematode" refers to a decrease in the numbers of living nematodes. The extent of reduction accomplished by a compound depends upon the application rate of the compound, the particular compound used, and the target species. At least a nematode-inactivating amount should be used. The term "nematode-inactivating amount" is used to describe the amount, which is sufficient to cause a measurable reduction in the treated nematode population.

The method is practiced in accordance with standard techniques for the application of nematicides. In general, good nematicidal activity can be expected at rates of 1–10 lbs/acre. The compound can be formulated as described below in the Compositions section. When formulated as dispersions, nematicides are typically applied as aqueous drenches around growing plants or applied incrementally via irrigation systems. When applied as granules, nematicides may be incorporated into the soil before planting, or applied in a band on top of a seed row, or broadcast and then incorporated into the soil, or used as a side dressing to an established crop.

Fungicide Utility

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Greenhouse Tests

The following experiments were performed in the laboratory to determine the fungicidal efficacy of the compounds of the invention.

The test compounds are formulated for application by dissolving 8 mg of the compound into 2 mL of acetone, using ultrasonication if necessary. A 0.5 mL aliquot of (8 mg/2 mL) sample is removed to a second container, leaving 6 mg/1.5 mL in the first container. 1.5 mL of acetone is added to the second container, the contents are mixed, and a 0.5 mL aliquot of (2 mg/2 mL) sample is removed to a third container, leaving 1.5 mg/1.5 mL in the second container. 1.5 mL of acetone is added to the third container, the contents are mixed, and a 0.5 mL aliquot of (0.5 mg/2 mL) sample is removed to a fourth container, leaving 0.375 mg/1.5 mL in the third container. 1.5 mL of acetone is added to the fourth container, the contents are mixed, and a 0.5 mL aliquot is removed and discarded, leaving 0.09375 mg/1.5 mL in the fourth container. To each of the four containers is added 13.5 mL of a 110 ppm solution of Triton X 100 in water. Final formulations contain 10% acetone, 100 ppm Triton X 100, and 400, 100, 25, and 6.25 ppm of test compound.

The formulated test compounds were applied by foliar spray. The following plant pathogens and their corresponding plants were employed.

| Pathogen | Designation in following Table | Host |
|---|---|---|
| *Erysiphe graminis tritici* (powdery mildew) | ERYSGT | wheat |
| *Pyricularia oryzae* (rice blast) | PYRIOR | rice |
| *Puccinia recondita tritici* (leaf rust) | PUCCRT | wheat |
| *Leptosphaeria nodorum* (glume blotch) | LEPTNO | wheat |
| *Plasmopara viticola* (downy mildew) | PLASVI | grape |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

The following table presents the activity of typical compounds of the present invention when evaluated in this experiment. The effectiveness of test compounds in controlling disease was rated using the following scale.

| | |
|---|---|
| 0 | = not tested against specific organism |
| – | = 0–19% control at 400 ppm |
| + | = 20–89% control at 400 ppm |
| ++ | = 90–100% control at 400 ppm |
| +++ | = 90–100% control at 100 ppm |

FUNGICIDE DATA

| COMPOUND NUMBER | ERYSGT | PYRIOR | PUCCRT | LEPTNO | PLASVI |
|---|---|---|---|---|---|
| 1 | – | ++ | ++ | ++ | ++ |
| 2 | + | + | ++ | ++ | ++ |
| 3 | +++ | + | ++ | ++ | ++ |
| 4 | + | + | +++ | +++ | + |
| 5 | + | – | – | + | + |
| 6 | + | +++ | + | +++ | ++ |
| 7 | + | – | + | + | +++ |
| 8 | ++ | +++ | + | +++ | +++ |
| 9 | +++ | +++ | ++ | ++ | +++ |
| 10 | +++ | +++ | ++ | ++ | +++ |
| 11 | +++ | ++ | ++ | +++ | + |
| 12 | +++ | ++ | ++ | +++ | +++ |
| 13 | ++ | + | ++ | + | +++ |
| 14 | ++ | + | + | ++ | ++ |
| 15 | + | ++ | ++ | ++ | ++ |
| 16 | + | + | ++ | ++ | +++ |
| 17 | + | ++ | ++ | ++ | ++ |
| 18 | 0 | ++ | ++ | ++ | + |
| 19 | – | ++ | ++ | ++ | ++ |
| 20 | 0 | ++ | ++ | ++ | ++ |
| 21 | 0 | + | ++ | ++ | ++ |
| 22 | 0 | ++ | ++ | ++ | ++ |
| 23 | 0 | 0 | 0 | 0 | 0 |
| 24 | 0 | + | ++ | ++ | + |
| 25 | 0 | + | ++ | ++ | ++ |
| 27 | – | – | – | – | – |
| 28 | + | – | + | – | – |
| 29 | + | + | + | ++ | ++ |
| 30 | +++ | ++ | ++ | + | 0 |
| 31 | ++ | + | + | + | 0 |
| 32 | ++ | ++ | ++ | +++ | 0 |
| 33 | – | – | + | – | 0 |
| 34 | – | – | – | – | 0 |
| 35 | + | +++ | ++ | + | 0 |
| 36 | – | + | ++ | ++ | 0 |
| 37 | +++ | +++ | – | ++ | 0 |
| 38 | ++ | +++ | – | +++ | 0 |
| 39 | +++ | +++ | ++ | – | 0 |
| 40 | + | + | ++ | ++ | 0 |
| 41 | +++ | ++ | ++ | – | 0 |
| 42 | ++ | ++ | ++ | ++ | 0 |
| 43 | +++ | ++ | ++ | + | 0 |
| 44 | +++ | ++ | ++ | + | 0 |
| 45 | +++ | ++ | ++ | + | 0 |
| 46 | + | – | – | – | 0 |
| 47 | +++ | ++ | ++ | ++ | 0 |
| 48 | +++ | + | ++ | + | 0 |
| 49 | + | + | ++ | + | 0 |
| 50 | +++ | ++ | ++ | ++ | 0 |
| 52 | 0 | 0 | 0 | 0 | 0 |
| 53 | ++ | ++ | ++ | +++ | +++ |
| 54 | – | – | + | – | +++ |
| 55 | +++ | ++ | ++ | +++ | ++ |
| 59 | + | + | ++ | +++ | +++ |

-continued

| | | | | | |
|---|---|---|---|---|---|
| 60 | + | + | ++ | ++ | +++ |
| 62 | ++ | ++ | ++ | +++ | +++ |
| 63 | +++ | +++ | ++ | +++ | +++ |
| 65 | + | ++ | 0 | ++ | ++ |
| 66 | +++ | + | ++ | +++ | +++ |
| 67 | +++ | + | ++ | +++ | +++ |
| 68 | − | + | − | ++ | − |
| 69 | +++ | +++ | ++ | ++ | +++ |
| 70 | +++ | +++ | ++ | +++ | +++ |
| 71 | +++ | +++ | ++ | +++ | +++ |
| 72 | +++ | ++ | ++ | +++ | +++ |
| 73 | ++ | + | ++ | +++ | +++ |
| 75 | − | + | ++ | ++ | +++ |
| 76 | − | ++ | ++ | +++ | +++ |
| 78 | − | − | ++ | − | +++ |
| 80 | +++ | +++ | ++ | − | +++ |

Compositions

The compounds of formula (1) or (2) are applied in the form of compositions which are important embodiments of the invention, and which comprise a compound of formula (1) or (2) and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of formula (1) and (2) can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
|---|---|
| Compound of formula (1) or (2) | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |
| B. 1.5 Emulsifiable Concentrate | |
| Compound of formula (1) or (2) | 18.50% |
| "TOXIMUL D" | 2.50% |
| "TOXIMUL H" | 2.50% |
| "EXXON 200" | 76.50% |
| C. 1.0 Emulsifiable Concentrate | |
| Compound of formula (1) or (2) | 12.50% |
| N-methylpyrrolidone | 25.00% |
| "TOXIMUL D" | 2.50% |
| "TOXIMUL H" | 2.50% |
| "EXXON 200" | 57.50% |
| D. 1.0 Aqueous Suspension | |
| Compound of formula (1) or (2) | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |
| E. 1.0 Aqueous Suspension | |
| Compound of formula (1) or (2) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| F. 1.0 Aqueous Suspension | |
| Compound of formula (1) or (2) | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |
| G. Wettable Powder | |
| Compound of formula (1) or (2) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| H. Granules | |
| Compound of formula (1) or (2) | 5.0% |
| propylene glycol | 5.0% |
| Exxon 200 | 5.0% |
| Florex 30/60 granular clay | 85.0% |

I claim:

1. A compound of the formula

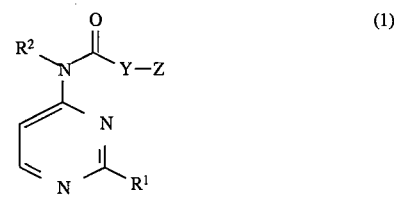

(1)

and N-oxides and salts thereof, wherein $R^1$ is H, $(C_1-C_4)$alkyl, $(C_3-C_4)$ branched alkyl, $(C_3-C_7)$ cycloalkyl, $(C_2-C_4)$ alkenyl, $(C_3-C_4)$ branched alkenyl, halo$(C_1-C_4)$alkyl, $(C_1-C_4)$alkoxy, $(C_1-C_4)$alkoxy$(C_1-C_4)$alkyl, halo$(C_1-C_4)$alkoxy, $(C_1-C_4)$alkylthio, $(C_1-C_4)$alkylsulfonyl, $(C_1-C_4)$alkylsulfinyl, halo, or phenyl;

$R^2$ is H, $(C_1-C_4)$alkyl, $(C_3-C_4)$ branched alkyl, $(C_1-C_4)$alkanoyl, halo$(C_1-C_4)$alkyl, $(C_1-C_4)$alkoxymethyl, $CH_2SiR^9R^{10}R^{11}$, hydroxymethyl, benzyl, $(C_3-C_6)$ cycloalkylmethyl, or

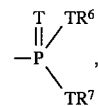

where $R^9$, $R^{10}$ and $R^{11}$ are independently $(C_1-C_4)$ alkyl, $(C_3-C_4)$ branched alkyl, phenyl, or substituted phenyl, each T is independently O or S, and $R^6$ and $R^7$ are independently $(C_1-C_4)$ alkyl, $(C_3-C_4)$ branched alkyl, phenyl, or substituted phenyl;

Y is —$CH_2$—,

Z is a phenyl group substituted in the 4-position with:
a) phenoxy,
b) substituted phenoxy,
c) halo $(C_2-C_4)$ alkoxy;

where substituted phenoxy refers to a phenoxy group wherein the phenyl ring is substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, substituted phenoxy, phenyl, substituted phenyl, $NO_2$, OH, CN, $(C_1-C_4)$ alkanoyl, benzoyl, $(C_1-C_4)$ alkanoyloxy, $(C_1-C_4)$alkoxycarbonyl, phenoxycarbonyl, or benzoyloxy, provided that a substituted phenyl, substituted phenyoxy, substituted phenylthio, or substituted phenylsulfonyl group that is itself substituted with a group from this list shall not, include a total of more than three phenyl rings.

2. A compound of claim 1 wherein Z is phenyl substituted with a halo($C_2$–$C_4$)alkoxy group.

3. A compound of claim 1 wherein Z is phenyl substituted with a phenoxy or substituted phenoxy group.

4. A compound having the formula (1A)

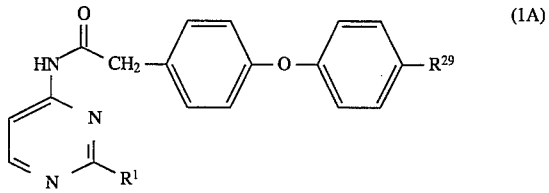

(1A)

where $R^1$ is ($C_1$–$C_4$) alkyl, ($C_3$–$C_4$) branched alkyl, or ($C_3$–$C_7$) cycloalkyl; and $R^{29}$ is an electron withdrawing group selected from the group consisting of halo, halo($C_1$–$C_4$)alkyl, ($C_1$–$C_4$) alkanoyl, CN, and $NO_2$.

5. A compound of claim 4 wherein $R^1$ is ethyl and $R^{29}$ is $CF_3$, CN, or Cl.

6. A compound selected from the group consisting of
1) 4-(4-chlorophenoxy)phenyl-N-(2-methyl-4-pyrimidinyl)acetamide;
2) 4-(4-cyanophenoxy)phenyl-N-(2-methyl-4-pyrimidinyl)acetamide;
3) 4-(2,2,2-trifluroethoxy)phenyl-N-(2-methyl-4-pyrimidinyl)acetamide;
4) 4-(2,2,2-trifluroethoxy)phenyl-N-(2-methylthio-4-pyrimidinyl)acetamide;
5) 4-(2,2,2-trifluroethoxy)phenyl-N-(2-phenyl-4-pyrimidinyl)acetamide;
6) 4-(4-fluorophenoxy)phenyl-N-(2-methylthio-4-pyrimidinyl)acetamide;
7) 4-(4-fluorophenoxy)phenyl-N-(2-phenyl-4-pyrimidinyl)acetamide;
8) 3-phenoxyphenyl-N-(2-methyl-4-pyrimidinyl)acetamide;
9) 4-(2,2,2-trifluroethoxy)phenyl-N-(2-ethyl-4-pyrimidinyl)acetamide;
10) 4-(4-fluorophenoxy)phenyl-N-(2-ethyl-4-pyrimidinyl)acetamide;
11) 4-(4-trifluoromethylphenoxy)phenyl-N-(2-ethyl-4-pyrimidinyl)acetamide;
12) 4-(4-cyanophenoxy)phenyl-N-(2-ethyl-4-pyrimidinyl)acetamide;
13) 4-(5-cyano-2-pyridinyloxy)phenyl-N-(2-ethyl-4-pyrimidinyl)acetamide;
14) 4-(5-bromo-2-pyrimidinyloxy)phenyl-N-(2-ethyl-4-pyrimidinyl)acetamide;
15) 4-(2,2,2-trifluroethoxy)phenyl-N-(2-cyclopropyl-4-pyrimidinyl)acetamide;
16) 4-(4-fluorophenoxy)phenyl-N-(2-cyclopropyl-4-pyrimidinyl)acetamide;
17) 4-(4-chlorophenoxy)phenyl-N-(2-ethyl-4-pyrimidinyl)acetamide;
18) 4-(2,2,2-trifluroethoxy)phenyl-N-(2-propyl-4-pyrimidinyl)acetamide;
19) 4-(4-fluorophenoxy)phenyl-N-(2-propyl-4-pyrimidinyl)acetamide;
20) 4-(2,2,2-trifluroethoxy)phenyl-N-(2-butyl-4-pyrimidinyl)acetamide;
21) 4-(4-fluorophenoxy)phenyl-N-(2-butyl-4-pyrimidinyl)acetamide;
22) 4-(2,2,2-trifluroethoxy)phenyl-N-(2-cyclobutyl-4-pyrimidinyl)acetamide;
23) 4-(4-fluorophenoxy)phenyl-N-(2-cyclobutyl-4-pyrimidinyl)acetamide;
24) 4-(2,2,2-trifluroethoxy)phenyl-N-(2-(1,1-dimethylethyl)-4-pyrimidinyl)acetamide;
25) 4-(4-fluorophenoxy)phenyl-N-(2-(1,1-dimethylethyl)-4-pyrimidinyl)acetamide;
27) 4-(4-fluorophenoxy)phenyl-N-(2-(1-methylethenyl)-4-pyrimidinyl)acetamide;
28) 4-(2,2,2-trifluroethoxy)phenyl-N-(4-pyrimidinyl)acetamide;
29) 4-(4-chlorophenoxy)phenyl-N-(2-cyclopropyl-4-pyrimidinyl)acetamide;
30) 4-(2,2,2-trifluroethoxy)phenyl-N-(2-(1-methylethyl)-4-pyrimidinyl)acetamide;
31) 4-(4-fluorophenoxy)phenyl-N-(2-(1-methylethyl)-4-pyrimidinyl)acetamide;
32) 4-(3-fluoro-5-trifluromethyl-2-pyridinyloxy)phenyl-N-(2-ethyl-4-pyrimidinyl)acetamide;
33) N-(2-ethyl-4-pyrimidinyl)-2 methyldecamide;
35) 5-(2,2,2-trifluoromethoxy)-2-pyridinyl-N-(2-ethyl-4-pyrimidinyl)acetamide;
36) 4-(5-methylsulfonyl-2-pyridinyloxy)phenyl-N-(2-ethyl-4-pyrimidinyl)acetamide;
37) 4-(5-chloro-2-pyridinyloxy)phenyl-N-(2-ethyl-4-pyrimidinyl)acetamide;
38) 4-(2,2,2-trifluroethoxy)phenyl-N-(2-(methoxymethyl)-4-pyrimidinyl)acetamide;
39) 4-(4-fluorophenoxy)phenyl-N-(2-(methoxymethyl)-4-pyrimidinyl)acetamide;
40) biphenyl-N-(2-ethyl-4-pyrimidinyl)acetamide;
41) 4-pentylphenyl-N-(2-ethyl-4-pyrimidinyl)acetamide;
42) 4-difluromethoxy-N-(2-ethyl-4-pyrimidinyl)acetamide;
43) 4-(2,2,3,3-tetrafluropropoxy)phenyl-N-(2-ethyl-4-pyrimidinyl)acetamide;
44) 4-butoxyphenyl-N-(2-ethyl-4-pyrimidinyl)acetamide;
45) 4-(1-methylethyl)phenyl-N-(2-ethyl-4-pyrimidinyl)acetamide;
46) 4-(1-methyl ethyl)phenoxy-N-(2-ethyl-4-pyrimidinyl)acetamide;
47) 4-phenoxyphenyl-N-(2-ethyl-4-pyrimidinyl)acetamide;
48) 4-(1,1-dimethylethyl)phenyl-N-(2-ethyl-4-pyrimidinyl)acetamide;
49) 4-(4-acetylphenoxy)phenyl-N-(2-ethyl-4-pyrimidinyl)acetamide;
50) 2-naphthyl-N-(2-ethyl-4-pyrimidinyl)acetamide;
51) 4-(4-chlorophenoxy)phenyl-N-cyclopropyl-N-methylacetamide;
53) 4-(4-nitrophenoxy)phenyl-N-(2-ethyl-4-pyrimidinyl)acetamide;
54) 4-(4-fluorophenoxy)phenyl-N-(2-chloro-4-pyrimidinyl)acetamide;
55) 4-(1,1,2,2-tetrafluoroethoxy)phenyl-N-(2-ethyl-4-pyrimidinyl)acetamide;
56) 4-(2,2,2-trifluoroethoxy)phenyl-N-(2-ethyl-4-pyrimidinyl)-N-methylacetamide;
57) 4-(2,2,2-trifluoroethoxy)phenyl-N-ethyl-N-(2-ethyl-4-pyrimidinyl)acetamide;
58) 4-(4-chlorophenoxy)phenyl-N-methyl-N-(2-ethyl-4-pyrimidinyl)acetamide;
59) 4-(4-chlorophenoxy)phenyl-N-(2-(1,1-dimethylethyl)-4-pyrimidinyl)acetamide;
60) 4-(4-cyanophenoxy)phenyl-N-(2-(1,1-dimethylethyl)-4-pyrimidinyl)acetamide;
61) 4-(4-chlorophenoxy)phenyl-N-ethyl-N-(2-ethyl-4-pyrimidinyl)acetamide;
62) 4-(4-trifluoromethylphenoxy)phenyl-N-(2-(1,1-dimethylethyl)-4-pyrimidinyl)acetamide;
63) 4-(4-trifluoromethylphenoxy)phenyl-N-(2-methyl-4-pyrimidinyl)acetamide;
64) 4-(1,1,2,2-tetrafluoroethoxy)phenyl-N-(2-ethyl-4-pyrimidinyl)-N-methylacetamide;

65) 4-(4-trifluoromethylphenoxy)phenyl-N-(2-butyl-4-pyrimidinyl)acetamide;
66) 4-(4-trifluoromethylphenoxy)phenyl-N-(2-cyclobutyl-4-pyrimidinyl)acetamide;
67) 4-(4-trifluoromethylphenoxy)phenyl-N-(2-cyclopropyl-4-pyrimidinyl)acetamide;
68) 4-(4-trifluoromethylphenoxy)phenyl-N-(4-pyrimidinyl)acetamide;
69) 4-(3-trifluoromethylphenoxy)phenyl-N-(2-methyl-4-pyrimidinyl)acetamide;
70) 4-(4-trifluoromethylphenoxy)phenyl-N-(2-(methoxymethyl)-4-pyrimidinyl)acetamide;
71) 4-(3-trifluoromethylphenoxy)phenyl-N-(2-cyclobutyl-4-pyrimidinyl)acetamide;
72) 4-(4-trifluoromethylphenoxy)phenyl-N-(2-(1-methylethyl)-4-pyrimidinyl)acetamide;
73) 3-(dimethylamino)-N-(2-ethyl-4-pyrimidinyl)-1-(4-(4-trifluoromethylphenoxy)phenyl)-2-propenamide;
74) 3-(dimethylamino)-N-(2-ethyl-4-pyrimidinyl)-1-(4-(1,1,2,2-tetrafluoromethoxy)phenyl)-2-propenamide;
75) 3-(ethylamino)-N-(2-ethyl-4-pyrimidinyl)-1-(4-(1,1,2,2-tetrafluoromethoxy)phenyl)-2-propenamide;
76) 3-(dimethylamino)-N-(2-ethyl-4-pyrimidinyl)-1-(4-(4-chlorophenoxy)phenyl)-2-propenamide;
77) 3-(ethylamino)-N-(2-ethyl-4-pyrimidinyl)-1-(4-(4-chlorophenoxy)phenyl)-2-propenamide;
78) 3-(dimethylamino)-N-(2-ethyl-4-pyrimidinyl)-1-(4-(4-cyanophenoxy)phenyl)-2-propenamide;
79) 3-(ethylamino)-N-(2-ethyl-4-pyrimidinyl)-1-(4-(4-cyanophenoxy)phenyl)-2-propenamide;
80) 3-(2-methylpropylamino)-N-(2-ethyl-4-pyrimidinyl)-2-(4-(4-cyanophenoxy)phenyl)-2-propenamide.

7. A pesiticidal composition which comprises a compound of claim 4 in combination with a phytologically acceptable carrier.

8. A method of inhibiting a nematode population which comprises applying to the locus of a nematode, a nematode inactivating amount of a compound of claim 4.

9. A method of inhibiting an insect or mite population which comprises applying to the locus of the insect or arachnid an effective insect or mite inactivating amount of a compound of claim 4.

10. A method of inhibiting plant pathogens which comprises applying an effective amount of a compound of claim 4 to a locus of the pathogen.

* * * * *